US006991820B2

(12) United States Patent
Ming et al.

(10) Patent No.: US 6,991,820 B2
(45) Date of Patent: Jan. 31, 2006

(54) COMPOSITION HAVING BACTERISTATIC AND BACTERICIDAL ACTIVITY AGAINST BACTERIAL SPORES AND VEGETATIVE CELLS AND PROCESS FOR TREATING FOODS THEREWITH

(75) Inventors: Xintian Ming, Cottage Grove, WI (US); William Robert King, Walnut Creek, CA (US); Jan Payne, Villa Park, IL (US)

(73) Assignee: Danisco A/S, Copenhagen (DK)

( * ) Notice: Subject to any disclaimer, the term of this patent is extended or adjusted under 35 U.S.C. 154(b) by 0 days.

(21) Appl. No.: 10/194,668

(22) Filed: Jul. 12, 2002

(65) Prior Publication Data

US 2003/0108648 A1 Jun. 12, 2003

Related U.S. Application Data

(60) Provisional application No. 60/305,114, filed on Jul. 13, 2001.

(51) Int. Cl.
*A23B 4/14* (2006.01)

(52) U.S. Cl. ......................... 426/310; 426/335; 426/532
(58) Field of Classification Search ................ 426/310, 426/326, 335, 532, 580, 615, 549, 643
See application file for complete search history.

(56) References Cited

U.S. PATENT DOCUMENTS 5,096,718 A * 3/1992 Ayres et al. .................... 426/9
5,260,061 A * 11/1993 Ayres et al. ................. 424/115
5,458,876 A * 10/1995 Monticello ................ 424/94.61
5,635,484 A * 6/1997 Ayres et al. .................... 514/18
5,639,659 A * 6/1997 Barefoot et al. .......... 435/252.1
5,989,612 A * 11/1999 King et al. .................. 426/335
6,132,786 A * 10/2000 Poulos et al. ................ 426/326
6,207,210 B1 * 3/2001 Bender et al. .............. 426/335
6,451,365 B1 * 9/2002 King et al. .................. 426/326
6,620,446 B2 * 9/2003 King et al. .................. 426/335
6,692,779 B2 * 2/2004 Dominques et al. .......... 426/61

FOREIGN PATENT DOCUMENTS

| EP | 0453860 | 10/1991 |
|----|---------|---------|
| EP | 0466244 | 1/1992 |
| WO | 95/08275 | 3/1995 |
| WO | 01/05254 | 1/2001 |

OTHER PUBLICATIONS

Patent Abstracts of Japan vol. 1995, No. 08, Sep. 29, 1995 & JP 07-115950, May 9, 1995.

* cited by examiner

*Primary Examiner*—Carolyn Paden
(74) *Attorney, Agent, or Firm*—Fay, Sharpe, Fagan, Minnich & McKee, LLP

(57) ABSTRACT

Antibacterial compositions effective against both gram positive and gram negative vegetative bacteria plus harmful gram positive sporeforming bacteria include propionibacterial metabolites in combination with two or more of the following: a lantibiotic; a lytic enzyme; and an organic acid or its salt. Methods of use are provided, as well as food products treated with these antibacterial compositions.

24 Claims, No Drawings

COMPOSITION HAVING BACTERISTATIC AND BACTERICIDAL ACTIVITY AGAINST BACTERIAL SPORES AND VEGETATIVE CELLS AND PROCESS FOR TREATING FOODS THEREWITH

This application claims the benefit under 35 U.S.C. § 119(e) of earlier filed and copending U.S. Provisional Application No. 60/305,114, filed Jul. 13, 2001, entitled "Food-Treating Composition Having Bacteristatic and Bactericidal Activity and Process for Treating Food Therewith", the contents of which are incorporated by reference herein.

BACKGROUND OF THE INVENTION

1. Field of the Invention

The present invention relates to a composition having bacteristatic and bactericidal activity against undesirable bacteria present in food, and to a process for treating food with such a composition in order to render the food more resistant to spoilage and safer for consumption.

2. Description of the Related Art

Processes and compositions for treating food products to prevent or inhibit bacterial spoilage and/or the development of harmful bacteria are widely practiced . It is a common practice in the commercial sterilization of low-acid foods (i.e., pH>4.5) to apply a combination of heat and pressure to canned or pouched foods sufficient to achieve at least a 12 decimal (12D) reduction of spores of *Clostridium botulinum*, considered the most heat resistant of dangerous bacteria in foods deriving from its ability to form highly heat resistant spores that survive lesser processes. Unfortunately, typical 12D sterilization processes can alter the appearance and flavor of foods, making them less desirable than foods that are processed at temperatures that are less lethal (sublethal) to spores of *C. botulinum*.

In recent years, more foods have been subjected to treatment with sublethal doses of heat, pressure, irradiation, ultrasound, or combinations thereof, which can decrease bacterial levels of a food product while also providing for a more organoleptically attractive food product. These sublethal processing treatments alter food products less dramatically than traditional 12D heat treatments used to sterilize food products, but most foods processed in this fashion must then be refrigerated to protect against the possible outgrowth of sporeforming bacteria.

While sublethal processing treatments kill most vegetative spoilage and pathogenic bacterial cells, they typically kill only a fraction of potential bacterial spores, which have elevated resistance to heat, irradiation and other treatments. Such spores can survive sublethal processing treatments and subsequently grow in the processed food, causing spoilage, illness and, in the worst cases, death. For this reason, most foods treated in this fashion are refrigerated so as to slow or prevent the growth of such spores.

Food products infected with these spore-forming bacteria are numerous and include, but are not limited to, ready to eat meals and entrees, deli salads, dairy foods, dressings and condiments, processed or cured meats, poultry, and seafood, as well as processed fruits and vegetables, fruit and vegetable derived products, grains and grain derived products, pastas, soups, and aseptically packaged foods. The long refrigerated shelf-life of ready to eat foods, especially vacuum packed, modified atmosphere packed (MAP), and canned food products, can be especially troublesome as it may allow the spores of some bacteria, such as *Clostridium botulinum*, to germinate and grow in the food with the production of lethal toxins. Such risk may be higher in sublethally processed foods because sublethal processes typically destroy the nonpathogenic vegetative species of bacteria that would otherwise spoil or compete with spore-forming species. A further exacerbating risk in this class of foods is the use of vacuum or modified atmosphere packaging processes, which produce the anaerobic conditions necessary for the development and growth of clostridial spores.

Extensive research has also been conducted in the field of food safety to develop food grade compositions which can function as antibacterial agents. Relevant prior art may be found in U.S. Pat. Nos. 5,096,718 and 5,260,061 and the references cited therein. These patents disclose the use of metabolites of propionic acid bacteria in certain foods to increase the shelf life of the resulting products. These metabolites demonstrate efficacy against gram negative bacteria but are typically not as effective against gram positive bacteria or their spores.

JP 07-115950 discloses the combination of bacteriocins produced by lactic acid bacteria of the propionibacteria genus in combination with either organic acids and their salts, fatty acid esters of polyhydric alcohols, amino acids, antibacterial peptides and proteins, polysaccharides comprising sugars, saccharic acids and amino sugars and their partial decomposition products, spices and their essential oils and plant components, and alcohols.

U.S. Pat. No. 5,217,250 discloses the use of nisin compositions as bactericides. Nisin is a lantibiotic, more specifically, a polypeptide with antimicrobial properties which is produced in nature by various strains of the bacterium *Streptococcus lactis*. Nisin is primarily effective against gram positive bacteria. This patent discloses that the combination of a chelating agent, such as EDTA or other acetate salts or citrate salts, with nisin can result in a broad range bactericide.

U.S. Pat. No. 5,458,876 discloses the combination of a lantibiotic with lysozyme as an antibacterial composition.

EP 0 466 244 discloses a composition having improved antibacterial properties which is a mixture of at least one of each of the following groups of compounds: (I) a cell wall lysing substance or a salt thereof, (II) an antibacterial compound, and (III) an adjuvant selected from organic acids acceptable for use in food products, preparations for cosmetic use or personal hygiene, or salts of these acids; phosphates and condensed phosphates or their corresponding acids; and other sequestering agents. Preferably (I) is lysozyme, (II) may be a bacteriocin (e.g. nisin or pediocin), and (III) may be acetic acid, lactic acid, citric acid, propionic acid, tartaric acid, orthophosphates, hexametaphosphates, tripolyphosphates, other polyphosphates, or sequestering agents containing substituted or non-substituted amino groups, e.g. EDTA.

EP 0 453 860 discloses the combination of nisin with a phosphate buffer effective at a pH of between 5.5 and 6.5 to help eradicate gram negative bacteria from surfaces.

U.S. Pat. No. 5,989,612 discloses the combination of a propionibacterial metabolite, not solely propionic acid, with a potentiator substance, which includes chelators, essential oils, or organic acids (other than propionic acid, acetic acid, lactic acid, and their respective salts).

U.S. Pat. No. 6,207,210 discloses the combination of a propionibacterial metabolite, not solely propionic acid, a lantibiotic, and one or more phosphate salts which act as a chelating agent.

It would still be beneficial to develop an antibacterial composition effective against both gram positive and gram negative bacteria, as well as against gram positive spores, especially in foods subjected to a sublethal (less than 12D) processing treatment.

SUMMARY OF THE INVENTION

It has now been discovered, quite surprisingly, that a food-treating composition containing at least one propionibacterial metabolite and at least two additional components selected from the group consisting of (a) lantibiotics, (b) lytic enzymes, and (c) organic acids and/or organic acid salts, demonstrates excellent bacteristatic and bactericidal activity against gram positive and gram negative vegetative bacteria, as well as gram positive sporeforming bacteria typically found on or in foods. This composition is especially effective in being both bacteristatic and bactericidal to potentially harmful food-borne pathogenic bacteria when used in conjunction with one or more sublethal processing treatments.

In particularly preferred embodiments, lantibiotic (a) of the composition herein is nisin or lacticin; lytic enzyme (b) is lysozyme or chitinase; and organic acid and/or salt of organic acid (c) is selected from the group consisting of acetic acid, an acetic acid salt such as sodium acetate, sodium diacetate, or potassium acetate, lactic acid, a lactic acid salt such as sodium lactate or potassium lactate, propionic acid, propionates, including but not limited to, sodium propionate and potassium propionate, citric acid, a citric acid salt such as sodium citrate or potassium citrate, or mixtures thereof.

In yet another embodiment, the present invention provides a process for reducing the overall bacterial count or population in or on a food by applying to the food a bacteristatic-effective and bactericidal-effective amount of the foregoing composition.

In an additional embodiment, the present invention provides a food product having a reduced live bacterial population as a result of having applied thereon a bacteristatic-effective and bactericidal-effective amount of the foregoing composition.

In practice, the composition of matter according to the present invention can be applied to a food in combination with one or more sublethal processing treatments such as sublethal heat treatment.

DETAILED DESCRIPTION OF THE PREFERRED EMBODIMENTS

The antibacterial composition of the present invention contains at least one propionibacterial metabolite and at least two additional components selected from the group consisting of (a) lantibiotics, (b) lytic enzymes and (c) organic acids and/or organic acid salts. The antibacterial composition demonstrates improved bacteristatic and bactericidal activity against undesirable gram positive and gram negative vegetative bacteria as well as gram positive spores typically found on or in foods.

As used herein, "metabolite" refers to an organic substance, other than water or carbon dioxide, produced by propionibacteria. "Bacteristatic" or "bacteristatic-effective" refers to the ability of a substance or composition to inhibit the outgrowth or multiplication of bacteria. "Bactericidal" or "bactericidal-effective" refers to the characteristic of a substance or composition to destroy, i.e., to kill, bacteria. The expressions "active metabolite" and "inhibitory metabolite" both refer to a bacteristatic metabolite.

"Lytic enzyme" includes any substance capable of degrading the bacterial cell wall resulting in lysis (and death) of the cell.

The expression "harmful bacteria" includes all bacterial organisms present in a food which cause, accelerate, participate in, or otherwise play a role in the spoilage of food and/or which may be deleterious to health, especially human health, if the bacteria or their byproducts (e.g., toxins) are ingested.

The term "food" or "food product" encompasses all edible nutritive substances and compositions, especially those intended for human consumption, and includes unprocessed, as well as processed, e.g., cooked, nutritive substances and compositions. The expression "present in food" refers to all external surfaces and interior surfaces and/or portions of a food that are resident to harmful bacteria.

For purposes of this invention, "sublethal treatment" is defined as any operation which is sufficient to significantly reduce the bacterial population of a food but which is insufficient to effect a 12 decimal (12D) reduction of spores of *C. botulinum*. Sublethal treatments that are contemplated herein include heat, irradiation, pressure, ultrasound, ozone, nitrite, etc. which, when applied to a food, will significantly reduce its bacterial count but will be insufficient to effect a 12 decimal (12D) reduction of spores of *C. botulinum*.

The first component of the food-treating composition of the present invention is a bacteristatic-effective amount of at least one propionibacterial metabolite. These metabolites are disclosed in U.S. Pat. Nos. 5,096,718 and 5,260,061, the contents of which are incorporated by reference herein. These metabolites can inhibit bacterial growth or multiplication, particularly in the case of gram negative bacteria. This effect can be achieved without resulting in an undesirable flavor, odor, or appearance, even in "delicately flavored" foods, which would detract from their acceptance.

The metabolite can be obtained by growing propionibacteria, e.g. *Propionibacterium shermanii, P. freudenreichii, P. pentosaceum, P. thoenii, P. arabinosum, P. rubrum, P. jensenii, P. peterssonii*, and related species (as identified in Malik et al., Can. J. Microbiol. 14:1185, 1968). *Propionibacterium* strains identified by number are available from the American Type Culture Collection (ATCC). Other cultures are widely available or can be obtained from Oregon State University, Corvallis, Oreg., without cost. For example, *Propionibacterium freudenreichii* subsp. *shermanii*, ATCC strain #9616, can be used in accordance with the present invention.

While propionic acid can be utilized in the present invention, it is generally known by those skilled in the art to impart a strong flavor to foods. While such flavors are desirable in some foods, such as Swiss cheese, in many foods they are undesirable. Whole fraction fermentate compositions containing other propionibacterial metabolites in a mixture demonstrate antibacterial activity without the strong flavors associated with propionic acid. Examples of such compositions containing these metabolites include those sold by Rhodia Inc. under the MICROGARD® trademark.

*Propionibacterium* cultures can be used to produce a food ingredient, including one or more metabolites, that can inhibit gram negative bacteria at the normal pH of many foods. The metabolites, which can be obtained as by-products of propionibacterial culture fermentation of skim milk or other suitable fermentation medium, can serve as flavor adjuncts and may also be inhibitory to a number of microorganisms after the conclusion of the fermentation. The degree of inhibition achieved for the mixtures of metabolites studied is greater than for propionic acid alone, favoring use of, e.g., the MICROGARD® compositions. The shelf-life of a food product is extended by providing in or on the product one or more of such active metabolites in combination with the other components of the composition of the present invention.

The growth medium for *Propionibacterium* species can be formulated with milk, whey, or dextrose, plus yeast extracts, protein hydrolysates, or any other protein containing stimulants. Various buffers, salts, acids, and other processing aids may be incorporated to enhance metobolite production and improve the handling of the final composition. The growth liquid, after development of the propionibacteria up to about $10^6$ to about $10^{10}$ cells per ml, can be heat treated (pasteurized) to kill the inoculated and adventitious bacteria prior to use of the metabolite containing growth media in a liquid, condensed, dried, or frozen form.

To facilitate storage and shipping, a propionibacteria growth mixture can be evaporated and frozen, or concentrated and dehydrated, e.g., by spray-drying, or freeze-drying, to form a powder. The metabolites may be separated or purified or used as a mixture. Powdered or liquid natural metabolites of propionibacteria can be incorporated into various foods and feeds to render them less susceptible to spoilage by growth and/or enzymatic activity of gram negative bacteria. The antispoilage activity can also be obtained by incorporating viable propionibacteria directly into the food.

In most instances, substantial improvement in bacterial reduction can be obtained by including in the antibacterial composition of matter of the present invention an amount of a propionibacterial metabolite sufficiently small that it will have no deleterious effect on the flavor or aroma of the food product. More specifically, the liquid, condensed, or dried product, which typically comprises pasteurized cultured solids or liquids containing the propionibacterial metabolites in addition to the other components of the antibacterial composition of matter of the present invention, is generally added to the food product so that the amounts of propionibacterial metabolites range from about 0.01 to about 2.0 percent by weight of the product, preferably from about 0.05 to about 1.0 percent by weight of the product, and more preferably from about 0.1 to about 0.75 percent by weight of the product. In the case where the composition of matter is added to a dry mix to which liquid ingredients are added and thereafter cooked, such as a cake, the amount added is by weight of the dry mix prior to cooking.

Commercially available materials, more specifically, pasteurized cultured solids or liquids including propionibacterial metabolites, are sold by Rhodia Inc. under the MICROGARD® trademark. These products are unpurified whole fraction fermentates of milk or similar media. MICROGARD® MG 100 is a pasteurized cultured skim milk that is standardized with skim milk solids and spray dried. MICROGARD® MG 200 is a pasteurized cultured dextrose that has been standardized with maltodextrin and spray dried. MICROGARD® MG 250 is a condensed (frozen or liquid) version of the cultured dextrose product.

The food-treating composition of the invention may also include a bactericidal-effective amount of at least one lantibiotic as a second component. The term "lantibiotics" was coined by Schnell et al. (Nature 333:276–278 (1988)) to describe a group of bactericidal substances which contain the amino acid lanthionine and other non-protein amino acids. The common properties of these bacteriocides are reviewed by Kellner et al. (Eur. J. Biochem 177:53–59 (1988)) wherein they note that " . . . polycyclic polypeptide antibiotics possess a high content of unsaturated amino acids (dehydroalanine, dehydrobutrine) and thioether amino acids (meso-lanthionine, (2S, 3S, 6R)-3-methyllanthionine). Furthermore, lysinoalanine, 3-hydroxyaspartic acid and S-(2-aminovinyl)-D-cystine are found in some members." Lantibiotics include nisin, subtilin, pep 5, epidermin, gallidermin, cinnamycin, Ro09-0198, duramycin and ancovenin. These ribosomally-synthesized peptide antibiotics contain from 19 to 34 amino acids and are produced by various microbes including *Staphylococcus* species, *Bacillus* species and *Streptomyces* species. In addition to their unique composition of non-protein amino acids, they can be distinguished from other polypeptide antibiotics on the basis of their specificity. Bacteriocins in general, and the lantibiotics in particular, are characterized by a very narrow spectrum of action. Thus, only a few species of bacteria are sensitive to a particular bacteriocin at practical concentrations. This is in contrast with other broad spectrum polypeptide antibiotics which are active against most bacteria, and the "lytic peptides" discussed by Jaynes et al. in published international application WO 89/00194, which are active against most bacteria, yeasts, and even mammalian cells.

Nisin, one of the most thoroughly characterized bacteriocins, is a ribosomally coded peptide which occasionally occurs as a dimer with a molecular weight of about 7000. Nisin is the collective name describing several closely related substances which exhibit similar amino acid compositions, and some limited range of antibiotic activity. This phenomenon is discussed by E. Lipinska in "Antibiotics and Antibiosis in Agriculture" (M. Woodbine, Ed.) pp. 103–130. It contains several unusual amino acids including beta-methyllanthionine, dehydroalanine, and lanthionine among its total of 34 amino acids. There are five unusual thio-ether linkages in the peptide which contribute to its stability in acid solutions. Nisin shares remarkable homology of structure and action with other lantibiotics, for example subtilin and epidermin (Buchman et al., J. Bio. Chem 263 (31): 16260–16266 (1988)). Recent reviews of nisin, its physical properties and uses include "Bacteriocins of Lactic Acid Bacteria", T. R. Klaenhammer, Biochimie 70:337–349 (1988), "Nisin", A. Hurst, Avd. Appl. Microbiol. 27:85–121 (1981), and U.S. Pat. No. 4,740,593.

The use of nisin to combat *L. monocytogenes* has been reported by M. Doyle; "Effect of Environmental and Processing Conditions on Listeria Monocytogenes", Food Technology, 42(4):169–171 (1988). This article describes the initial inhibition of the organism's growth (for about 12 hours) and reports that *L. monocytogenes* may grow at a pH level as low as 5.0 and is resistant to alkaline pH with the ability to grow at pH 9.6.

By itself, nisin is not as effective an antimicrobial in complex media such as foods. For example, it is known that nisin activity against *C. botulinum* typically decreases in complex media such as foods. (Rogers and Montville, J. Food Sci., 59(3):663–668 (1994).)

Nisin is commercially available from Rhodia Inc. in a standardized 2.5 weight percent preparation under the trademark Novasin™. Where nisin is added as a component of the antibacterial composition of the present invention, it can be present in amounts ranging from about 0.5% to about 10% by weight of the antibacterial composition.

Lantibiotics containing protein may also be present as a low level fermentation by-product in certain varieties of cheddar or American cheese and in the fermented skim milk product known as MICROGARD® MG300. Where a lantibiotic is added to the antibacterial composition of the present invention in the form of a fermented milk product such as MICROGARD® MG300, the amounts of MICRO- GARD® MG300 utilized can range from about 75% to about 95% by weight of the antibacterial composition.

In practice, where a lantibiotic is used as a component of the antibacterial composition of the present invention, the lantibiotic is added to the food product such that it is present in amounts ranging from about 1 to about 100 ppm (by weight of the food product) of active ingredient (e.g., nisin), with preferred levels ranging from about 1 to about 12.5 ppm, based on safety and suitability of use in different foods.

As alternatives to the lantibiotics described above, a *Pediococcus* bacterial metabolite, specifically pediocin, can yield efficacious results in the composition of the present invention. In addition, the new class of streptococcal bacteriocins called lacticins, especially lacticin 3147 as described in WO 96/32482, should produce similar activity against gram positive bacteria. Both pediocins and lacticins primarily have bacteristatic activity against a limited range of gram positive bacteria.

In a preferred embodiment, nisin or lacticin are used as the lantibiotic in the composition of matter of the present invention.

Another component of the antibacterial composition of the present invention can be a cell wall lysing substance such as a lytic enzyme. These enzymes may be used to control or prevent the growth of target microorganisms. For a lytic enzyme to be useful in the food industry as an antibacterial component or agent, it should be capable of degrading a broad spectrum of bacteria, particularly those that cause food spoilage and/or are pathogens.

In a preferred embodiment, a lysozyme is used as the lytic enzyme. Lysozymes (muramidase; mucopeptide N-acetyl-mucamoylhydrolase; 1,4-beta-N acetylhexosaminodase, E.C. 3.2.1.17) are well-known lytic enzymes which have been isolated from various sources and are well characterized enzymes. Lysozymes are most commonly derived from egg albumin in a food grade extraction process, but are also available from arctic scallops, human milk, tears, and other natural sources. First discovered in 1922 by W. Fleming, egg white lysozyme was among the first proteins sequenced, the first for which a three dimensional structure was suggested using x-ray crystallography, and the first for which a detailed mechanism of action was proposed. Its antimicrobial activity against gram positive bacteria is well documented, for example by V. N. Procter et al. in CRC Crit. Reviews in Food Science and Nutrition, 26(4):359–395 (1988). The molecular weight of egg white lysozyme is approximately 14,300 to 14,600, the isoelectric point is pH 10.5–10.7. It is composed of 129 amino acids which are interconnected by four disulfide bridges. Similar enzymes have been isolated and characterized from other sources including such diverse producers as *Escherichia coli* and human tears. Despite slight differences (for example, the human lysozyme has 130 amino acids) the capacity for hydrolysis of acetylhexosamine polymers remains essentially the same. Accordingly, for purposes of this invention, the term lysozyme is intended to include those cell wall or peptidoglycan degrading enzymes which have the ability to hydrolyze acetylhexosamine and related polymers.

Lysozyme is known to kill or inhibit the growth of bacteria and fungi, and is used in Europe to control the growth of the spoilage organism *Clostridium tyrobutyricum* in a wide variety of cheeses. It has also been proposed for use in a variety of other food preservation applications and has been reported to inhibit the growth of (and in some cases kill) *Listeria monocytogenes* (Hughey et al, Appl. Environ. Microbiol 53:2165–2170 (1987)). Lysozyme derived from egg albumin with an activity of about 20,000 Shugar units/mg is commercially available from Rhodia under the trademark NovaGARD™.

When lysozyme is used as an antimicrobial in food, it is added to the food product in amounts ranging from about 20 to about 500 ppm by weight of the solution used for treatment, more preferably between about 50 to about 200 ppm, primarily to inhibit *Clostridum tyrobutyricum* in ripened cheeses. Lysozyme is not bactericidal at these levels against other gram positive bacteria, but it has been used at higher levels (greater than 1000 ppm, typically 2000 ppm or more) to remove the cell wall from a wide range of gram positive bacteria.

Where lysozyme is added as a component of the antibacterial composition of the present invention, it can be present in amounts ranging from about 0.25% to about 10% by weight of the antibacterial composition. Preferably, where lysozyme is used as a component of the antimicrobial composition of the present invention, it is present in amounts ranging from about 50 ppm to about 150 ppm by weight of a food product treated with the composition of the present invention.

Another preferred lytic enzyme that may be used in the composition of matter in accordance with the present disclosure is chitinase.

The antibacterial composition of matter may also contain organic acids acceptable for use in food products or salts of these acids. The antibacterial composition of matter may contain individual acids or salts, or mixtures thereof. Preferred organic acids or salts for use in the composition of matter include acetic acid, sodium acetate, sodium diacetate, potassium acetate, lactic acid, sodium lactate, potassium lactate, propionic acid, propionates, including, but not limited to, sodium propionate and potassium propionate, citric acid or its salts such as sodium citrate or potassium citrate, or mixtures thereof. In a more preferred embodiment, sodium diacetate is used in amounts ranging from about 1% to about 25% by weight of the antibacterial composition. Preferably, the resulting food product treated,with the antimicrobial composition of the present invention will have from about 500 ppm to about 1500 ppm sodium diacetate.

Other additives which can be present in the inventive composition include, but are not limited to, the following materials: additional antibacterial and/or chelating agents, natural or synthetic seasonings and/or flavors, dyes and/or colorants, vitamins, minerals, nutrients, enzymes, and binding agents such as guar gum, xanthan gum, and the like. The addition of these materials is not considered critical to the success of the present invention and would be considered within the skill of the artisan.

In a particularly preferred embodiment, the antimicrobial composition of matter includes a propionibacterial metabolite mixed with a variety of organic acids, or their salts, including sodium diacetate, in combination with both a lantibiotic bacteriocin, such as nisin or lacticin, and a lytic enzyme, such as lysozyme, to control the growth of a broad range of gram positive and gram negative spoilage and/or sporeforming bacteria in food products.

The antimicrobial composition of the present invention may be used in connection with any food product which is susceptible to bacterial growth or degradation. These include, but are not limited to, dairy foods, fruits and vegetables, fruit and vegetable derived products, grains and grain derived products, meats, poultry, and seafood. A preferred embodiment includes the treatment of sublethally processed food products including ready to eat meals, entrees, and meats, deli salads, dressings (including salad dressings), sauces and condiments, pastas, soups, and aseptically packaged foods, as well as mixtures of the foregoing.

The antimicrobial composition according to the present invention is most readily used by mixing with and/or applying on a blendable food product, but could also be effective to treat the surface of solid food products by a dip, rinse, or spray, or by application to the interior of such products, e.g. by injection. In other embodiments, the antibacterial composition may be applied as a marinade, breading, seasoning rub, glaze, colorant mixture, and the like, or as an ingredient to be mixed with and incorporated into the food product, the key criteria being that the antimicrobial composition be available to the surface (including internal surfaces) subject to bacterial growth and/or degradation. In still other embodiments, the antimicrobial composition may be indirectly placed into contact with the food surface by applying the composition to food packaging materials and thereafter applying the packaging to the food surface such that the antibacterial composition comes into contact with the external food surface. The optimum amount to be used will depend upon the antibacterial composition of the particular food product to be treated and the method used to apply the antibacterial composition to the food surface, but can be determined by simple experimentation.

The antimicrobial compositions of the present disclosure are effective against gram positive bacteria including, but not limited to, anaerobic sporeforming bacteria including clostridial species such as *Clostridium botulinum, Clostridium perfringens, Clostridium sporogenes, Clostridium tyrobutyricum,* and *Clostridium putrefasciens*; aerobic sporeforming bacteria including bacilli species such as *Bacillus cereus, Bacillus licheniformis, Bacillus subtilis,* and *Bacillus coagulans*; gram positive vegetative pathogens including staphylococci species such as *Staphylococcus aureus*; listerial species such as *Listeria monocytogenes*; and, finally, spoilage producing vegetative bacteria from the *Micrococcus, Streptococcus* and lactic acid groups including, but not limited to, *Lactobacillus* and *Leuconostoc* species.

The antimicrobial compositions of the present disclosure are also effective against gram negative bacteria including, but not limited to, *Escherichia* bacteria such as *E. coli* H7:0157; *Campylobacter* bacteria such as *Campylobacter jejuni*; *Vibrio* bacteria such as *Vibrio parahaemolytica*; *Pectobacteria* such as *Pectobacterium carotovorum*; *Pseudomonas* bacteria such as *Pseudomonas fluorescens*; and *Salmonella* species.

It has been further discovered that the composition of matter in accordance with the present disclosure is effective in reducing the live bacterial content of food products containing more than about 1% fat, lipid, or oil soluble materials, as well as food products that are fatty emulsions. Where the food product is a fat in water emulsion, it is particularly advantageous to incorporate the composition of matter into the aqueous phase of the food product in order to minimize partitioning into the lipid phase where the composition would be unavailable for antibacterial protection of the food product.

Food products treated with the composition of matter in accordance with the present disclosure may also be treated with sublethal processing treatments such as heat, irradiation, pressure, ultrasound, freezing, pulsed electric field, ozone, nitrite, etc. It has been found that the composition of matter in combination with a sublethal processing treatment is more effective in reducing the live bacterial content of food products than either treatment alone. These food products remain stable at ambient temperatures for about 3 days or longer. At refrigerated temperatures, these food products remain stable for about 7 days or longer.

The following non-limiting examples are illustrative of the broad range of antimicrobial compositions that may be used to preserve food products in accordance with the present disclosure.

EXAMPLES

The following examples compare the effectiveness of an antibacterial composition, referred to as CB-1, in nonfat dry milk (NFDM) with Nisin (Novasin™) as a control. CB-1 contained Novasin™, MICROGARD® MG 200, sodium diacetate, and lysozyme. The components of these compositions are set forth below in Table 1.

TABLE 1

Antibacterial Compositions

| | % in blends | | | | |
|---|---|---|---|---|---|
| Blend | Novasin ™ | MG-200 ® | Na diacetate | Lysozyme | NFDM |
| Control | 8 | 0 | 0 | 0 | 92 |
| CB-1 | 2 | 87 | 10 | 1 | 0 |

Example 1

Inhibition of Antibacterial Composition Against *Bacillus cereus* in Whole and Skim Milk at 30° C.

Whole and skim milk was sterilized, 2,3,5-Tripheryltetrazolium chloride (TTC) was added (for indicating growth by color change), and the resulting mixture was inoculated with spores of *Bacillus cereus* (an aerobic sporeformer) at about 4–5 log cells/ml. The antibacterial composition (CB-1) and a Novasin™ control (Control) were added as 10% stock solutions (the Control contained 4 times the amount of nisin as CB-1). The inhibition was indicated by the minimal concentration for no growth during a given time and is set forth below in Table 2.

TABLE 2

Effectiveness of Compositions

| Treatment | MIC* (% of antibacterial composition required for no growth) | Novasin ™ concentration (ppm) |
|---|---|---|
| In whole milk | | |
| Control | >4 | >3200 |
| CB-1 | 3 | 600 |
| In skim milk | | |
| Control | 0.5 | 400 |
| CB-1 | 2 | 400 |

*MIC = minimum inhibition concentration

The plate count of *B. cereus* for these compositions was then obtained on TSA agar plates, incubated at 30° C. for 24 hours, and the results are indicated in Table 3 below.

TABLE 3

Plate counts
Inhibition against *B. cereus* in whole milk

| Treatment | CFU/ml |
| --- | --- |
| Control | 3 × 10e8 |
| Novasin | 5 × 10e6 |
| CB-1 | 1 × 10e4 |

Example 2

Inhibition of Antibacterial Composition Against *L. monocytogenes* in Whole and Skim Milk at 25° C.

Whole and skim milk was sterilized, 2,3,5-Tripheryltetrazolium chloride (TTC) was added (for indicating growth by color change), and the resulting mixture was inoculated with *L. monocytogenes* ATCC 19115 (a vegetative, gram positive pathogen) at about 4–5 log cells/ml. The antibacterial composition (CB-1) and Novasin™ control (Control) were added as 10% stock solutions (the Control contained 4 times the amount of nisin as CB-1). The inhibition was indicated by the minimal concentration for no growth during a given time and is set forth below in Table 4.

TABLE 4

Effectiveness of Compositions

| Treatment | MIC* (% of antibacterial composition required for no growth) | Novasin ™ concentration (ppm) |
| --- | --- | --- |
| In whole milk | | |
| Control | 4 | 3200 |
| CB-1 | 2 | 400 |
| In skim milk | | |
| Control | 0.5 | 400 |
| CB-1 | 1 | 100 |

*MIC = minimum inhibition concentration

The plate count of *L. monocytogenes* for these compositions was then obtained on TSA agar plates, incubated at 30° C. for 24 hours and the results are indicated in Table 5 below.

TABLE 5

Plate counts

| Treatment blend (ppm) | CFU**/ml day-2 at 3% | Novasin ™ conc. in 3% |
| --- | --- | --- |
| In whole milk | | |
| Non-treated control | 2.4 × 10e8 | 0 |
| Control | 5.6 × 10e7 | 2400 |
| CB-1 | 5 × 10e5 | 600 |
| In skim milk | day-2 at 0.5% | day-5 at 0.5% |
| Non-treated control | 1.6 × 10e8 | 2.0 × 10e8 |
| Control | 1800 | 2.0 × 10e5 |
| CB-1 | 1.1 × 10e6 | 1.0 × 10e3 at 2%* |

*2% CB-1 contains same conc. of Nisin as Control at 0.5%
**CFU = colony forming units (# of cells)

Example 3

Inhibition of Antibacterial Composition Against *C. sporogenes*, in Whole Milk at 30° C.

Whole milk was sterilized, 2,3,5-Tripheryltetrazolium chloride (TTC) was added (for indicating growth by color change), and the resulting mixture was inoculated with *C. sporogenes* (an anaerobic, nonpathogenic sporeformer) at about 4–5 log cells/ml. The antibacterial composition (CB-1) and a Novasin™ control (Control) were added as 10% stock solutions (the Control contained 4 times the amount of nisin as CB-1). The plate count of *C. sporogenes* for these compositions was then obtained on TSA agar plates, incubated at 30° C. for 24 hours and the results are indicated in Table 6 below.

TABLE 6

| Treatment | CFU/ml |
| --- | --- |
| Control | 2 × 10e8 |
| Novasin | 6 × 10e6 |
| CB-1 | 2 × 10e4 |

Example 4

Efficacy of Antibacterial Composition for Delaying Toxin Production in Food Products Ten strain mixtures of proteolytic *C. botulinum* spores (anaerobic, sporeforming pathogens), having about 100 spores/gram, were heat shocked at 88° C. for 10 minutes with foods. Some of the foods had a high fat content, and included an Alfredo sauce, a ready to eat meal (cooked chicken breast in sauce), a ready to eat soup, and a fresh pasta. The inoculated food samples were incubated at 15° C. or 27° C. The antibacterial composition (CB-1), Novasin™, and in one case CB-1 without lysozyme, were added as 10% stock solutions (the Novasin™ treatment contained the same amount of nisin as CB-1 and CB-1 without lysozyme). Untreated food samples were used as a control (Control). Triplicate samples were assayed at time 0 and each sampling interval, which varied depending upon the particular food being treated, its pH, its temperature, etc. Standard mouse assays were used to test for the presence of botulinal toxin, which was confirmed by ABE trivalent botulinal antitoxin. The efficacy of these antibacterial compositions in delaying toxin production in these food products is set forth below in Tables 7–10.

TABLE 7

Efficacy of antibacterial composition in delaying
toxin production in Alfredo sauce at pH 5.2, 27° C.

| Treatment | Days for toxin production |
| --- | --- |
| Control | 9–15 |
| CB-1 | >60 |

TABLE 8

Efficacy of antibacterial composition in delaying
toxin production in RTE meal at pH 5.6, 27° C.

| Treatment | Days for toxin production |
| --- | --- |
| Control | 7–10 |
| Novasin* | 13–20 |
| CB-1 | >30 |

*The Novasin treated simple had the same amount of nisin as the CB-1 treated sample.

TABLE 9

Efficacy of antibacterial composition in delaying
toxin production in RTE soup at pH 6.5, 15° C.

| Treatment | Days for toxin production |
| --- | --- |
| Control | 12–18 |
| Novasin** | 12–18 |
| CB-1-no lysozyme | 12–18 |
| CB-1 | 18–25 |

**The Novasin treated sample had the same amount of nisin as the CB-1 treated sample and the CB-1-no lysozyme treated sample.

TABLE 10

Efficacy of antibacterial composition in delaying
toxin production in fresh pasta at pH 6.0, 27° C.

| Treatment | Days for toxin production |
| --- | --- |
| Control | <10 |
| CB-1 | >20 |

It will be understood that various modifications may be made to the embodiments disclosed herein. Therefore the above description should not be construed as limiting, but merely as exemplifications of preferred embodiments. For example, various combinations of the components of the antibacterial composition described herein, and its use in various food products, will be apparent from or reasonably suggested by the foregoing description of the present invention. Those skilled in the art will envision other modifications within the scope and spirit of the claims appended hereto.

What is claimed is:

1. A food-treating composition having bacteristatic and bactericidal activity for harmful bacteria in food, said composition comprising at least one propionibacterial metabolite in combination with:
    a) a lantibiotic;
    b) a lytic enzyme; and,
    c) an organic acid or its salt;
wherein the organic acid or its salt is sodium diacetate.

2. The composition of matter according to claim 1 wherein said lantibiotic is selected from the group consisting essentially of nisin and lacticin.

3. The composition of matter according to claim 1 wherein the lytic enzyme is selected from the group consisting essentially of lysozyme and chitinase.

4. The composition of matter according to claim 1 further comprising one or more components selected from the group consisting of additional antibacterial agents, chelating agents, natural seasonings, synthetic seasonings, flavors, dyes, colorants, vitamins, minerals, nutrients, enzymes, and binding agents.

5. A process for inhibiting the growth of and killing bacteria on a food product, said process comprising a step of applying to one or more surfaces of said food product a bacteria growth-inhibiting and bactericidal effective amount of a composition of matter which demonstrates growth inhibitory and bactericidal efficacy against both gram positive and gram negative bacteria comprising a propionibacterial metabolite in combination with:
    a) a lantibiotic;
    b) a lytic enzyme; and,
    c) an organic acid or its salt;
wherein the organic acid or its salt is sodium diacetate.

6. The process according to claim 5 wherein the composition of matter reduces the amount of gram positive bacteria in the food product.

7. The process according to claim 6 wherein the gram positive bacteria is selected from the genera consisting of *Bacillus, Clostridia, Staphyloccus, Listeria, Micrococcus, Streptococcus, Lactobacillus* and *Leuconostoc*.

8. The process according to claim 7 wherein the bacteria is selected from the group consisting of *Bacillus cereus, Bacillus licheniformis, Bacillus subtilis, Bacillus coagulans, Clostridium botulinum, Clostridium perfringens, Clostridium sporogenes, Clostridium tyrobutyricum, Clostridium putrefasciens, Staphylococcus aureus* and *Listeria monocytogenes*.

9. The process according to claim 5 wherein the composition of matter reduces the amount of gram negative bacteria in the food product.

10. The process according to claim 9 wherein the gram negative bacteria is selected from the genera consisting of *Escherichia, Campylobacter, Vibrio, Pectobacteria, Pseudomonas*, and *Salmonella*.

11. The process according to claim 10 wherein the bacteria are selected from the group consisting of *E. coli* H7:0157, *Campylobacter jejuni, Vibrio parahaemolytica, Pectobacterium carotovorum*, and *Pseudomonas fluorescens*.

12. The process according to claim 5 wherein the food product is selected from the group consisting of dairy foods, fruits, vegetables, fruit derived products, vegetable derived products, grains, grain derived products, meats, poultry, seafood, ready to eat meals, deli salads, salad dressings, condiments, pastas, soups, aseptically packaged foods, and mixtures thereof.

13. The process according to claim 5 wherein the food product contains more than about 1% fat, lipid, or oil soluble materials.

14. The process according to claim 5 wherein the composition of matter is either applied to a surface of the food product or applied to a food packaging material which is thereafter brought into contact with the surface of the food product.

15. The process according to claim 5 wherein the composition of matter is applied to the food product by dipping, rinsing, injecting, spraying, or mixing.

16. The process according to claim 5 wherein the composition of matter is applied to the food product as a component of a marinade, breading, seasoning rub, glaze, or colorant mixture.

17. The process according to claim 5 wherein the food product comprises a fatty emulsion.

18. A process for inhibiting the growth of and killing bacteria on a food product which comprises a fatty emulsion, said process comprising incorporating a bacterial growth-inhibiting and bactericidal effective amount of a composition of matter which demonstrates growth inhibitory and bactericidal efficacy against both gram positive and gram negative bacteria into the aqueous phase of the fatty emulsion of said food product, said composition comprising a propionibacterial metabolite in combination with:

a) a lantibiotic;

b) a lytic enzyme; and, c) an organic acid or its salt.

19. A process for inhibiting the growth of and killing bacteria on a food product, said process comprising a step of applying to one or more surfaces of said food product a bacterial growth-inhibiting and bactericidal effective-amount of a composition of matter which demonstrates growth inhibitory and bactericidal efficacy against both gram positive and gram negative bacteria comprising a propionibacterial metabolite in combination with:

a) a lantibiotic;

b) a lytic enzyme; and, c) an organic acid or its salt;

wherein the organic acid or its salt is sodium diacetate; and the composition of matter being used in combination with a sublethal processing treatment of the food product.

20. The process according to claim 19 wherein the sublethal processing treatment is selected from the group consisting of heat, gamma irradiation, high pressure, ultrasound, ozone, nitrite and combinations thereof.

21. A food product having a reduced live bacterial population as a result of having applied thereon to one or more of its surfaces a composition of matter which demonstrates efficacy against both gram positive and gram negative bacteria comprising a propionibacterial metabolite in combination with:

a) a lantibiotic;

b) a lytic enzyme;

c) an organic acid or its salt.

wherein the organic acid or its salt is sodium diacetate.

22. The food product according to claim 21 which is selected from the group consisting of dairy foods, fruits, vegetables, fruit derived products, vegetable derived products, grains, grain derived products, meats, poultry, seafood, ready to eat meals, deli salads, salad dressings, condiments, pastas, soups, aseptically packaged foods, and mixtures thereof.

23. The food product according to claim 21 wherein the sublethal processing treatment is selected from the group consisting essentially of heat, gamma irradiation, high pressure, ultrasound, ozone, nitrite and combinations thereof.

24. The food product according to claim 21 wherein the composition of matter is used in combination with a sublethal processing treatment of the food product.

* * * * *